(12) United States Patent
Bedard et al.

(10) Patent No.: US 9,883,798 B2
(45) Date of Patent: Feb. 6, 2018

(54) SIMULTANEOUS CAPTURE OF FILTERED IMAGES OF THE EYE

(71) Applicants: Noah Bedard, San Francisco, CA (US); Lingfei Meng, Redwood City, CA (US); Vipin Namboodiri, Bangalore (IN); Krishna Prasad Agara Venkatesha Rao, Bangalore (IN); Kathrin Berkner, Los Altos, CA (US)

(72) Inventors: Noah Bedard, San Francisco, CA (US); Lingfei Meng, Redwood City, CA (US); Vipin Namboodiri, Bangalore (IN); Krishna Prasad Agara Venkatesha Rao, Bangalore (IN); Kathrin Berkner, Los Altos, CA (US)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/542,064

(22) Filed: Nov. 14, 2014

(65) Prior Publication Data
US 2016/0135682 A1    May 19, 2016

(51) Int. Cl.
*A61B 3/12* (2006.01)
*A61B 3/14* (2006.01)

(52) U.S. Cl.
CPC . *A61B 3/12* (2013.01); *A61B 3/14* (2013.01)

(58) Field of Classification Search
CPC .... A61B 3/14; A61B 3/10; A61B 3/12; A61B 3/107; A61B 3/117
USPC ........................................................ 351/206
See application file for complete search history.

(56) References Cited

U.S. PATENT DOCUMENTS

| | | | |
|---|---|---|---|
| 7,936,392 B2 | 5/2011 | Ng et al. | |
| 8,109,634 B2 | 2/2012 | Gil | |
| 8,243,157 B2 | 8/2012 | Ng et al. | |
| 2009/0137908 A1* | 5/2009 | Patwardhan | A61B 5/0059 600/476 |
| 2009/0143685 A1* | 6/2009 | Elner | A61B 3/10 600/476 |
| 2009/0225277 A1 | 9/2009 | Gil | |
| 2011/0261321 A1* | 10/2011 | Ramella-Roman | A61B 5/14555 351/206 |
| 2012/0182438 A1* | 7/2012 | Berkner | G01J 3/36 348/222.1 |
| 2012/0226480 A1 | 9/2012 | Berkner et al. | |
| 2013/0010260 A1* | 1/2013 | Tumlinson | A61B 3/152 351/206 |
| 2013/0235261 A1* | 9/2013 | Berkner | H04N 5/2254 348/374 |

(Continued)

FOREIGN PATENT DOCUMENTS

| | | |
|---|---|---|
| CN | 103932661 A | 7/2014 |
| EP | 2528321 A2 | 11/2012 |
| EP | 2769666 A1 | 8/2014 |

OTHER PUBLICATIONS

Dehoog, E. et al., "Snapshot Polarimeter Fundus Camera," Applied Optics, Mar. 20, 2009, pp. 1663-1667, vol. 48, No. 9.

(Continued)

*Primary Examiner* — Jordan Schwartz
(74) *Attorney, Agent, or Firm* — Fenwick & West LLP

(57) ABSTRACT

A multimode fundus camera enables three-dimensional and/or spectral/polarization imaging of the interior of the eye to assist in improved diagnosis.

18 Claims, 4 Drawing Sheets
(1 of 4 Drawing Sheet(s) Filed in Color)

(56) References Cited

U.S. PATENT DOCUMENTS

| | | | |
|---|---|---|---|
| 2014/0152983 A1* | 6/2014 | Masuda | G01J 3/513 356/302 |
| 2014/0206979 A1* | 7/2014 | Berkner | A61B 1/227 600/407 |
| 2014/0268041 A1* | 9/2014 | Copland | A61B 3/102 351/206 |
| 2014/0350379 A1* | 11/2014 | Verdooner | A61B 5/0059 600/407 |
| 2015/0146082 A1* | 5/2015 | Kim | H04N 5/2254 348/360 |
| 2015/0215604 A1* | 7/2015 | Tosic | H04N 17/002 348/46 |
| 2015/0250381 A1* | 9/2015 | Bedard | A61B 1/227 600/200 |
| 2015/0373316 A1* | 12/2015 | Meng | H04N 13/0239 348/47 |

OTHER PUBLICATIONS

Fukuma, Y. et al., "Retinal Nerve Fiber Layer Retardation Measurements Using a Polarization-Sensitive Fundus Camera," Journal of Biomedical Optics, Jul. 2011, pp. 076017-1-076017-6, vol. 16, No. 7.

Gao, L. et al., Snapshot Hyperspectral Retinal Camera with the Image Mapping Spectrometer (IMS), Biomedical Optics Express, Jan. 1, 2012, pp. 48-54, vol. 3, No. 1.

Johnson, W.R. et al., Snapshot Hyperspectral Imaging in Ophthalmology, Journal of Biomedical Optics, Jan./Feb. 2007, pp. 014036-1-014036-7, vol. 12, No. 1.

Mordant, D.J. et al., "Spectral Imaging of the Retina," Eye, 2011, pp. 309-320, vol. 25.

Ramella-Roman, J.C. et al., "Measurement of Oxygen Saturation in the Retina with a Spectroscopic Sensitive Multi Aperture Camera," Optics Express, Apr. 28, 2008, vol. 16, No. 9.

A Spectroscopic Sensitive Multi Aperture Camera, Optics Express, Apr. 28, 2008, vol. 16, No. 9.

European Partial Search Report, European Application No. 15194112.7, Mar. 17, 2016, 7 pages.

Chinese First Office Action, Chinese Application No. 201510779340.3, Dec. 5, 2016, 17 pages.

* cited by examiner

SIMULTANEOUS CAPTURE OF FILTERED IMAGES OF THE EYE

BACKGROUND OF THE INVENTION

1. Field of the Invention

This invention relates generally to imaging of the eye, for example spectral, polarization and/or three-dimensional imaging of the retina.

2. Description of the Related Art

Specialized cameras are used by optometrists, ophthalmologists, and other medical professionals to record images of the interior surface of the eye. During a routine physical examination, a handheld ophthalmoscope is often used to quickly view the fundus. Additional camera attachments can be used to record digital images from handheld ophthalmoscopes, allowing acquired images to be saved, manipulated, and reevaluated at future examinations. However, these images are limited by brightness, field-of-view, motion blur, and resolution, which restrict their diagnostic abilities for many diseases.

More complex imaging systems (e.g., fundus camera) can provide the clinician with better image quality, leading to more accurate diagnosis, screening, and monitoring treatment of eye pathologies. Conventional fundus cameras provide an image of the fundus with 2 to 5× magnification, with a field-of-view of 15 to 140 degrees. The device typically incorporates specialized illumination optics to shine light onto the interior surface of the eye. An eyepiece can be used to allow the clinician to view the interior of the eye. An electronic sensor can be used for digital acquisition of images. During an examination, the medical professional inspects the interior of the eye for abnormalities such as retinal tearing, thinning, unhealthy vasculature, opacity, occlusions, enlarged or reduced anatomy, and discoloration.

However, conventional fundus cameras have several drawbacks. First, in many cases, absolute measurements of anatomical features would be beneficial to determine the type and severity of disease. However, conventional fundus cameras produce a two-dimensional image of the three-dimensional eye. This makes it difficult or impossible to assess absolute measurements of area, depth or volume for the three-dimensional anatomy. Second, in many cases, spectral, polarization or other imaging modalities would also be beneficial. Conventional fundus cameras typically might capture different filtered images sequentially in time. Snapshots taken at different times must then be registered with each other. However, since the eye is constantly moving, this introduces a registration problem. In a different approach, it is possible to modify conventional fundus cameras to capture multiple filtered images in a single snapshot, for example by using multiple sensor arrays. However, this makes the camera more complex and expensive, and the multiple optical paths must be aligned to each other to ensure correct image registration.

Therefore, there exists a need for improved imaging systems to allow the simultaneous capture of three-dimensional, spectral, polarization and other modality images.

SUMMARY OF THE INVENTION

In one aspect, a multimode imaging system includes a first imaging subsystem, a filter module and a second imaging subsystem. The first imaging subsystem includes an objective lens, which is positionable in front of an eye to form an optical image of an interior of the eye (e.g., of the retina of the eye). The filter module, which includes multiple filters, is positioned at a pupil plane of the first imaging subsystem. The second imaging subsystem includes a microimaging array and a sensor array. The microimaging array (e.g., a microlens array) is positioned at the image plane of the first imaging subsystem, and the sensor array is positioned at a conjugate of the pupil plane. The sensor array captures a plenoptic image of the interior of the eye, which contains images of the interior of the eye filtered by each of the plurality of filters. In alternate embodiments, the system may include relay optics, allowing components to be positioned at conjugates of the image plane and pupil plane respectively.

Another aspect is an after-market conversion kit for converting a conventional fundus camera to a multimode imaging system as described above.

Other aspects include methods, devices, systems, and applications related to the approaches described above and its variants.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention has other advantages and features which will be more readily apparent from the following detailed description and the appended claims, when taken in conjunction with the accompanying drawings, in which:

Figure 1:
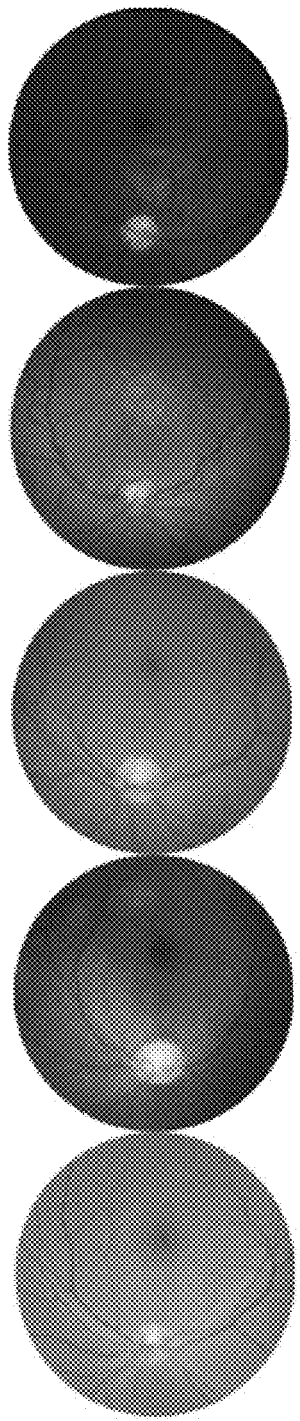
FIG. 1 (prior art) are example images showing different conditions of the eye.

The figures depict embodiments for purposes of illustration only. One skilled in the art will readily recognize from the following discussion that alternative embodiments of the structures and methods illustrated herein may be employed without departing from the principles described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed. To facilitate understanding, identical reference numerals have been used where possible, to designate identical elements that are common to the figures.

FIG. 1 (prior art) are example images showing different conditions of the eye. The images are images of the retina. The entries below each retina image list the disease condition, the features that can be used to diagnose the disease, and the modalities that would be useful to image the features. The leftmost column is a healthy eye.

The first disease listed is glaucoma, which has a clinical presentation of an enlarged optic disc. In order to assess enlargement of the optic disc, a medical professional might attempt to estimate the cup-to-disc ratio, as indicated in the second row of the table. He might do this by comparing current images of the retina to images from previous exams, by comparing optic disc symmetry between eyes, or by looking for thinning of the disc rim. In a conventional fundus camera, these rough measurements of a three-dimensional eye are estimated from a two-dimensional image. The analysis would be more accurate if they were estimated from a three-dimensional image instead, as indicated by the 3D modality listed in the third row of the table. In addition, the optic disc in a patient with glaucoma can also respond differently to polarized light. Increased intraocular pressure, retinal thinning, and changes in the optic disc can change birefringence properties or cause other polarization-related effects. These changes can be assessed by polarization images, as indicated by the polarization modality in the third row of the table. Conventional fundus cameras typically do not provide such polarization measurements.

Eye diseases can also change the vascular structure and physiological activity of the tissue, which alters the metabolism of tissue areas. For example, the second disease listed in FIG. 1 is diabetic retinopathy. This disease is classified by the type and severity of lesions, including: microaneurysms, hemorrhages, cotton wool spots, and venous beading. Three-dimensional measurement of these lesions could help objectively assess the severity of disease. Additionally, spectral imaging can indicate health of the retinal tissue by use of narrowband filters. In this approach, two or more narrowband spectral filters are selected based on the known spectral response of oxy-hemoglobin. Images acquired with these spectral filters are then used to generate an oxygen saturation map of the tissue. This oximetry map provides an additional clinical measurement of the tissue, which can greatly aid in diagnosis. Conventional fundus cameras do not provide such measurements.

The diagnosis of the third and fourth diseases listed in FIG. 1 would similarly be improved by three-dimensional, spectral, and/or polarization measurements.

Figure 2A:
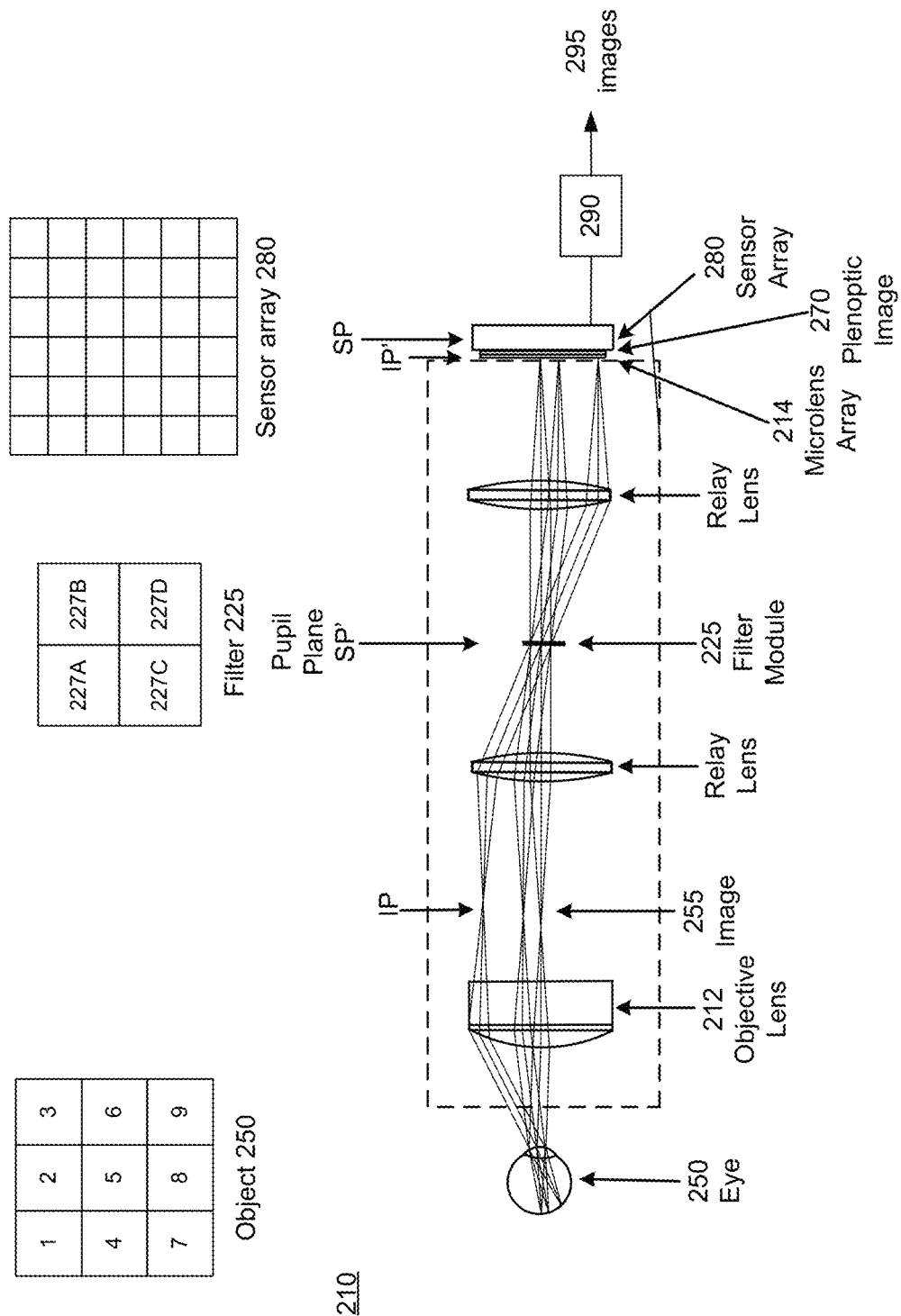
FIGS. 2a-b are diagrams illustrating an example of a multimode imaging system.
Figure 2B:
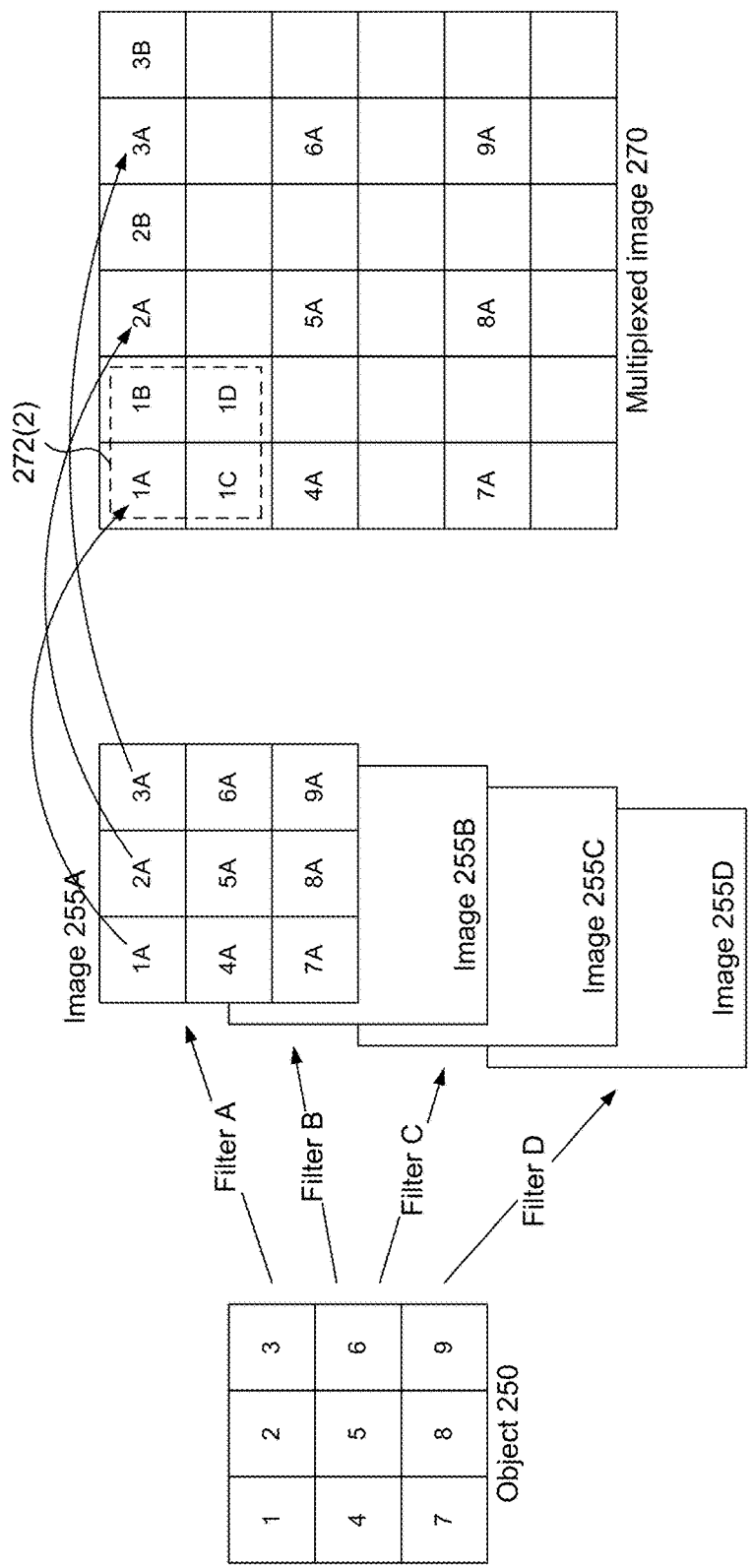

FIGS. 2a-b are diagrams illustrating an example of a multimode imaging system. The imaging system 210 includes an objective lens 212 (represented by a single lens in FIG. 2a), a secondary imaging array 214 (an array of image forming elements) and a sensor array 280. For convenience, the imaging optics 212 is depicted in FIG. 2a as a single optical element, but it should be understood that it could contain multiple elements.

The secondary imaging array 214 may be referred to as a microimaging array. The secondary imaging array 214 and sensor array 280 together may be referred to as a plenoptic sensor module. In this example, the secondary imaging array 214 is a microlens array. Other examples of microimaging arrays 214 include microlens arrays, arrays of pinholes, micromirror arrays, checkerboard grids and waveguide/channel arrays. The microimaging array 214 can be a rectangular array, hexagonal array or other types of arrays.

These components form two overlapping imaging subsystems. In the first imaging subsystem, the objective lens 212 is positionable in front of the eye 250 and forms an optical image 255 of the eye (retina, in this example) at the primary image plane IP, which may be relayed to conjugate planes such as the image port IP'. This imaging subsystem has a pupil plane. In the second imaging subsystem, the secondary imaging array 214 images the pupil plane onto the sensor array 280. To do this, the microimaging array 214 is located at the image plane IP or one of its conjugate planes. In this example, the microlens array 214 is located at conjugate plane IP'. The system in its entirety forms spatially multiplexed and interleaved optical images 270 at the sensor plane SP.

A filter module 225 is positioned at a plane SP' conjugate to the sensor plane SP. The actual physical location may be before, after or in the middle of the imaging optics 212. The filter module contains a number of spatially multiplexed filters 227A-D. In this example, the filter module 225 includes a rectangular array of filters 227, as shown in the bottom portion of FIG. 2a. The filter module 225 could contain spectral filters, polarization filters, neutral density filters, clear filters (i.e., no filters) or combinations of these.

The top portion of FIG. 2a provides more detail. In this diagram, the retina 250 is divided into a 3×3 array of regions, which are labeled 1-9. The filter module 225 is a 2×2 rectangular array of individual filters 227A-D. For example, each filter 227A-D may have a different spectral response. The sensor array 280 is shown as a 6×6 rectangular array.

FIG. 2b illustrates conceptually how the spatially multiplexed optical images 270A-D are produced and interleaved at sensor array 280. The object 250, if captured and filtered by filter 227A, would produce an optical image 255A. To distinguish filtered optical image 255A from an unfiltered image of the object, the 3×3 regions are labeled with the suffix A: 1A-9A. Similarly, the object 250 filtered by filters 227B,C,D, would produce corresponding optical images 255B,C,D with 3×3 regions labeled 1B-9B, 1C-9C and 1D-9D. Each of these four optical images 255A-D is filtered by a different filter 227A-D within filter module 225 but they are all produced simultaneously by the imaging system 210. This allows different modality images to be captured in a single snapshot, eliminating the need to later compensate for eye movement when registering images.

The four optical images 255A-D are formed in an interleaved fashion at the sensor plane, as shown in FIG. 2B. Using image 255A as an example, the 3×3 regions 1A-9A from optical image 255A are not contiguous in a 3×3 block within optical image 270. Rather, regions 1A, 1B, 1C and 1D, from the four different optical images, are arranged in a 2×2 fashion in the upper left of optical image 270 (the inversion of image 270 is neglected for clarity). Regions 1-9 are similarly arranged. Thus, the regions 1A-9A that make up optical image 270A are spread out across the composite optical image 270, separated by portions of the other optical images 270B-D. Put in another way, if the sensor is a rectangular array of individual sensor elements, the overall array can be divided into rectangular subarrays 271(1)-(9) of sensor elements (only one subarray 271(1) is shown in FIG. 2B). For each region 1-9, all of the corresponding regions from each filtered image are imaged onto the subarray. For example, regions 1A, 1B, 1C and 1D are all imaged onto subarray 271(1). Note that since the filter module 225 and sensor array 280 are located in conjugate planes, each imaging element in array 214 forms an image of the filter module 225 at the sensor plane SP. Since there are multiple imaging elements, multiple images 271 of the filter module 225 are formed.

The multiplexed image 270 can be processed by processing module 290 to reconstruct desired images of the object. The processing could be deinterleaving and demultiplexing. It could also include more sophisticated image processing. In addition to experiencing different filtering, the image data captured by system 210 also reflects different viewpoints. That is, the multiplexed images are captured from different viewpoints. This information can be used to reconstruct a three-dimensional image of the retina or to reduce the effects of occlusions. Thus, the reconstructed images 295 can include three-dimensional information in addition to filtered images (e.g., color and/or polarization images). The system could be designed so that it is switchable between a depth mode and a multi-filter mode. Alternately, the system can capture both depth and spectral/polarization information simultaneously.

For example, oxygen saturation of the retina can help predict diabetic retinopathy. Retinal oximetry can be measured with two or more spectral filters: one or more filters are selected at wavelengths where oxy/deoxy-hemoglobin spectra are most separated (such as anywhere between 600-700 nm), and one at an isosbestic point (such as 586 nm or 808 nm). For example, the system might use one filter centered at 548 nm with a 10 nm width (close to isosbestic) and a second filter centered at 610 nm with a 10 nm width. Additionally, near infrared wavelengths can be used to increase contrast of vasculature, especially deep vessels.

Regarding polarization, in practice, the illumination light may be polarized and tuned to account for birefringence of the cornea. For the analysis of reflected light, unpolarized, linear, and circular polarized filters can be used to assess polarization-dependent properties of the retina. Rods and cones maintain the polarization of incident light. In a healthy retina, the optic disc has no rods/cones and therefore causes depolarization of reflected light. Disease associated with malformed anatomy or increased intraocular pressure (glaucoma) can alter birefringence properties and polarization response in those areas.

Depth information can be used to more accurately estimate the size of the optic disc for glaucoma diagnosis. Without consideration of the optic disc size, the cup size and cup/disc ratio are not clinically meaningful. Current methods are typically qualitative or relative measurements. However, absolute measurement of the optic disc provides a quantitative feature for disease classification. Three-dimensional information may also be used to identify or measure physical deformations.

It should be noted that FIG. 2 has been simplified to illustrate underlying concepts. For example, the object 250 was artificially divided into an array in order to more easily explain the overall imaging function. As another example, most practical systems will use significantly larger arrays, particularly at the sensor array and possibly also at the filter module. In addition, there need not be a 2:1 relationship between the 6×6 regions at the sensor plane and the underlying sensor elements in the sensor array. Each region could correspond to multiple sensor elements, for example. As a final example, the regions labeled 1 in the object, 1A in the filtered image 255A and 1A in the composite image 270 do not have to be exact images of each other. In some designs, region 1A within image 270 may capture the filtered energy approximately from region 1 in the object 250, but it may not actually be an image of region 1. Thus, the energy collected by sensor elements in region 1A of image 270 may be integrating and sampling the image (or some transformation of the image) in region 1 in object 250, rather than representing a geometrical reproduction of the object at that region. In addition, effects such as parallax, vignetting, diffraction and optical propagation may affect any image formation.

The approach shown in FIG. 2 has several advantages. First, multiple optical images 270A-D are captured simultaneously at the sensor plane. Second, each captured image is filtered by a filter 227A-D within the filter module 225, and each filter 227 may be designed to implement different filtering functions. For convenience, the light distribution incident on the sensor array 280 will be referred to as a multi-filter plenoptic image 270, and the effect of the filter module may be referred to as filter-coding. In addition, since the filter module 225 is located at a conjugate plane SP' rather than the actual sensor plane SP, and since this typically means that the filter module will be much larger compared to what would be required at the sensor plane, the tolerances and other mechanical requirements on the filter module are relaxed. This makes it easier to manipulate the filter module, compared to if the filter module were located at the sensor plane (e.g., if attached to the sensor assembly).

Referring to FIG. 2a, note that the optical elements inside the dashed box (excluding the filter module 225) form a conventional fundus camera. The image port IP' of a conventional fundus camera typically is coupled to either an eyepiece to allow human viewing or to a detector array to capture images. The conventional fundus camera can be converted to the multimode imaging system shown by adding the filter module 225 at the pupil plane SP' and by coupling the image port IP' to a plenoptic sensor module (i.e., secondary imaging array 214 plus sensor array 280). However, to do this, the interior of the conventional fundus camera must be accessible in order to insert the filter module 225.

Figure 3:
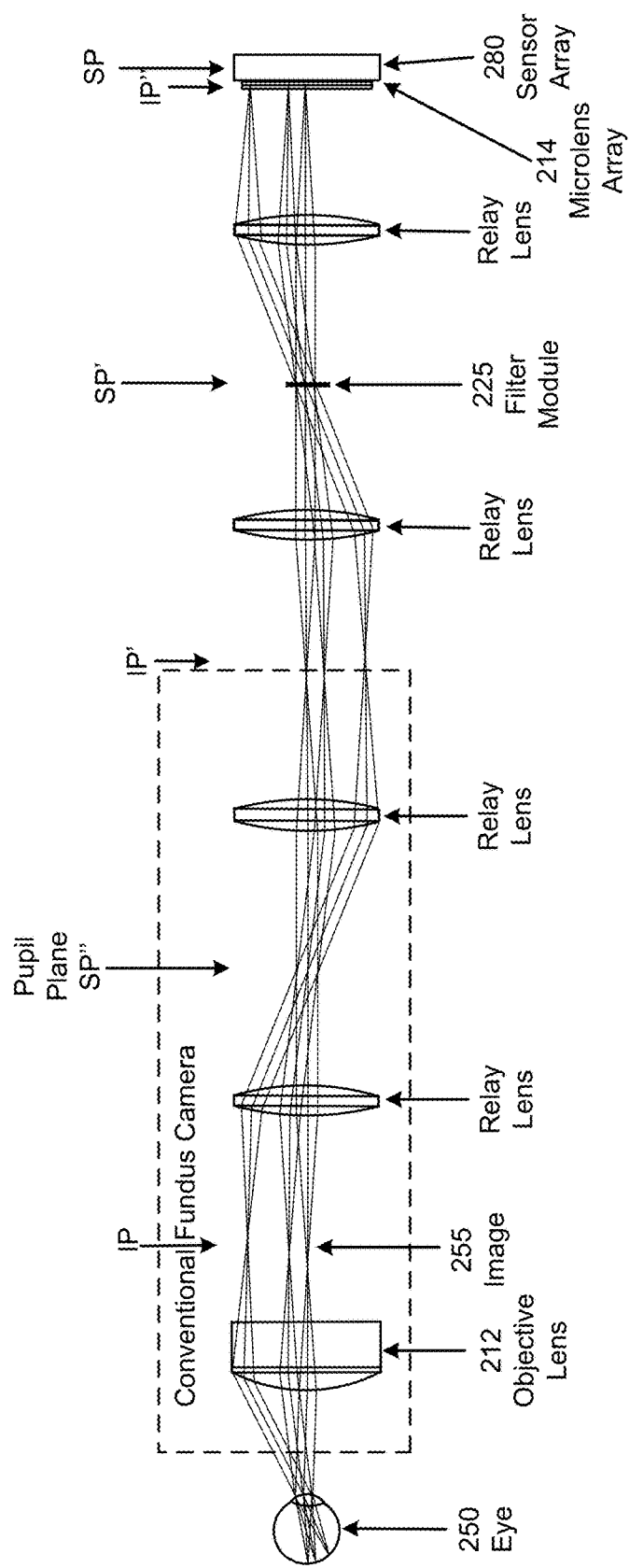
FIG. 3 is a diagram of an example of another multimode imaging system.

FIG. 3 is a diagram of an example of another multimode imaging system. In this example, the filter module 225 is positioned external to a conventional fundus camera. The conventional fundus camera itself is not modified. Instead, additional relay optics create a conjugate to the pupil plane and the filter module 225 is positioned in this conjugate plane. The microlens array 214 is positioned at a conjugate to the primary image plane IP and image port IP'. The sensor array 280 is positioned with the same spacing relative to the microlens array 214, as in FIG. 2a.

The following are some design considerations, using the system of FIG. 2a as an example. This system must work within the anatomical constraints of the human eye. In general, the eye has a depth of approximately 22 mm, a pupil size of 2-8 mm, and an aqueous medium of n=1.33. Accommodated at infinity, the f-number of the eye ranges from approximately 1.8 (at a pupil diameter of 8 mm) to 7.3 (at a pupil diameter of 2 mm).

Now assume a plenoptic sensor module with 100 µm pitch between microlenses, with 1 mm focal length in quartz with n=1.46. In this design, the volume between the microlens and sensor array is quartz. This corresponds to an f-number of f/#=f/(nD)=1/(1.46*0.1)=7. A standard fundus camera typically provides 2.5-5× magnification. A fundus camera imaging a fully dilated pupil would image at <4× magnification (7/1.8) in order to match the f-number of the lenslet array. For a partially dilated pupil (5 mm), the camera would image at <2.5× magnification (7/2.9).

A standard fundus camera images a 30 degree field-of-view at 2.5× magnification. This 30 degrees corresponds to approximately 9 mm diameter of the fundus. Thus, the image created by the fundus camera is approximately 22.5 mm diameter. Further assume a sensor array 280 with size of 24×36 mm. In that case, the entire image would fall onto the sensor area. Also assume that the microlens array sampling of the image in this case is 225 lenslets across the image diameter. The lateral resolution may be limited by lenslet sampling. For example, a 9 mm image sampled by 225 lenslets will result in Nyquist-limited resolution of 80 µm. Desired fundus image resolution is 15 µm/pixel (30 µm lateral resolution), although this number varies widely by reporting agency. This resolution can be achieved by using more closely spaced lenses, or by processing the images to increase the overall resolution. However, magnification, sampling, f-number, and field-of-view can be additionally adjusted using a secondary image relay between the fundus camera and plenoptic sensor module, as shown in FIG. 3. For example, if a dilated pupil creates an f-number that is too small to match the lenslet f-number, an aperture at a pupil plane can be reduced until the f-numbers match.

Depth resolution can be estimated as follows. Assume a fundus size of 9 mm, 5 mm pupil, and 2.5× magnification. Assume a microlens array with 100 µm lenslets on a sensor with 5.5 µm pixel pitch. Simulation shows an approximate depth resolution of 0.25 mm. For eye imaging, a 0.25 mm depth resolution should be sufficient to accurately measure fundus curvature.

In another wavefront sensing mode, a multimodal fundus camera is used to image the anterior segment of the eye. In this mode, the plenoptic camera acts as a wavefront sensor that detects aberrations in the optical wavefront passing through the anterior structures of the eye. Aberrations can be associated with anterior eye conditions, such as corneal ulcers, cataracts, and refractive errors (i.e. myopia, hyperopia, and astigmatism). The illumination in this mode can be traditional fundus illumination, illumination from a point source, or illumination from collimated light.

In a multimode imaging system, it is also possible to include a view finder to enable the examiner to view an image through the view finder at the time of image capture. A beam splitter or a single lens reflex can be used to split the optical path and direct the image to the plenoptic sensor module and to the view finder. For example, either a single lens reflex or a beam splitter may be inserted at the relay plane (as shown in FIG. 2a or 3) to allow a medical expert to look at the retina, while the plenoptic image of the retina is captured on the sensor array of the same device.

In other embodiments, a multimode imaging system may include a set of different filter modules. Each filter module may be used for a different purpose. For example, one filter module may be used for spectral imaging, while another filter module may be used for depth imaging. Different filter modules can be inserted into the device.

The multimode imaging systems described can be designed and manufactured as original instruments. Alternately, existing fundus cameras can be modified to become multimode. In one embodiment, an after-market conversion kit may be used to convert a conventional fundus camera to a multimode fundus camera. The conversion kit includes a plenoptic sensor module with a microimaging array and a sensor array. The original fundus camera is equipped with a conventional sensor. During the conversion, the plenoptic sensor module replaces the conventional sensor, such that the microimaging array (e.g., a microlens array or a pinhole array) is positioned at an image plane of the conventional fundus camera. For example, the microimaging array may be positioned at the plane where the conventional sensor was previously located.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. A multimode fundus imaging system comprising:
    a first fundus imaging subsystem comprising an objective lens, the first fundus imaging subsystem characterized by a field of view, magnification and working distance to form an optical image of a fundus of an eye when the first fundus imaging subsystem is positioned in front of the eye, the optical image formed at an image plane of the multimode fundus imaging system;
    a filter module positioned at a pupil plane of the first fundus imaging subsystem or at a conjugate thereof, the filter module comprising a plurality of filters; and
    a second imaging subsystem comprising a microlens array and a sensor array, the microlens array positioned at the image plane of the multimode fundus imaging system, and the sensor array positioned at a conjugate of a position of the filter module, the sensor array capturing a plenoptic image of the fundus of the eye, the plenoptic image containing images of the fundus of the eye filtered by each of the plurality of filters;
    wherein the system is operable in a depth imaging mode, in which the plenoptic image captured by the sensor array is processed to provide a three-dimensional image of the inside of the eye; and wherein the system is switchable between (a) the depth imaging mode in which the plenoptic image captured by the sensor array is processed to provide the three-dimensional image of the inside of the eye, and (b) a multi-filter imaging mode in which the plenoptic image captured by the sensor array is processed to provide two or more different filtered images of the inside of the eye.

2. The multimode fundus imaging system of claim 1 wherein the filter module comprises a plurality of different spectral filters.

3. The multimode fundus imaging system of claim 2 wherein the different spectral filters are selected to detect diabetic retinopathy.

4. The multimode fundus imaging system of claim 2 wherein the different spectral filters are selected to detect oxy-hemoglobin.

5. The multimode fundus imaging system of claim 4 wherein the filter module comprises a first spectral filter at wavelengths for which the oxy/deoxy-hemoglobin spectra are separated and a second spectral filter at a wavelength for an isosbestic point.

6. The multimode fundus imaging system of claim 5 wherein the first spectral filter has a passband in the 600-700 nm range.

7. The multimode fundus imaging system of claim 5 wherein the second spectral filter is a narrow bandpass filter centered around approximately 586 nm.

8. The multimode fundus imaging system of claim 5 wherein the second spectral filter is a narrow bandpass filter centered around approximately 808 nm.

9. The multimode fundus imaging system of claim 2 wherein the different spectral filters include an infrared filter.

10. The multimode fundus imaging system of claim 1 wherein the filter module comprises a plurality of different polarization filters.

11. The multimode fundus imaging system of claim 10 wherein the different polarization filters are selected to detect the optical disc of the eye.

12. The multimode fundus imaging system of claim 10 wherein the different polarization filters are selected to detect glaucoma.

13. The multimode fundus imaging system of claim 1 wherein:

the filter module comprises a plurality of different spectral filters and a clear filter, and the filter module is translatable relative to the first fundus imaging subsystem; and switching between the depth imaging mode and the multi-filter imaging mode comprises translating the filter module so that the clear filter is illuminated when the system is used in the depth imaging mode and the spectral filters are illuminated when the system is used in the multi-filter imaging mode.

14. The multimode fundus imaging system of claim 1 wherein the system is further operable in (c) a wavefront sensing mode, in which the system acts as a wavefront sensor to detect aberrations in the optical wavefront passing through anterior structures of the eye.

15. The multimode fundus imaging system of claim 1 wherein the first fundus imaging subsystem is a conventional fundus camera that produces a single two-dimensional optical image of the fundus of the eye, and the microlens array and sensor array are part of an after-market conversion kit used to convert the conventional fundus camera to the multimode fundus imaging system.

16. The multimode fundus imaging system of claim 15 wherein the filter module is positioned within the conventional fundus camera at the pupil plane of the conventional fundus camera.

17. The multimode fundus imaging system of claim 15 further comprising relay optics, wherein the filter module is positioned external to the conventional fundus camera at a conjugate of the pupil plane of the conventional fundus camera.

18. The multimode fundus imaging system of claim 1 wherein the first fundus imaging subsystem is characterized by a field of view, magnification and working distance to form an optical image of approximately a 9 mm diameter of the fundus of the eye.

* * * * *